United States Patent [19]

Morimoto et al.

[11] Patent Number: 4,694,086
[45] Date of Patent: Sep. 15, 1987

[54] GUANIDINE DERIVATIVES

[75] Inventors: Hiroshi Morimoto, New York, N.Y.; Akio Ohura, Aichi, Japan

[73] Assignee: Toray Industries, Inc., Tokyo, Japan

[21] Appl. No.: 848,373

[22] PCT Filed: Mar. 28, 1985

[86] PCT No.: PCT/JP85/00151
§ 371 Date: Mar. 26, 1986
§ 102(e) Date: Mar. 26, 1986

[87] PCT Pub. No.: WO86/05782
PCT Pub. Date: Oct. 9, 1986

[51] Int. Cl.⁴ ............................................ C07C 129/12
[52] U.S. Cl. .................................................... 564/236
[58] Field of Search ......................................... 564/236

[56] References Cited
U.S. PATENT DOCUMENTS
3,499,927  3/1970  Badcock et al. .................... 564/236

Primary Examiner—Paul J. Killos
Assistant Examiner—L. Hendriksen
Attorney, Agent, or Firm—Austin R. Miller

[57] ABSTRACT

The novel guanidine derivative compounds having a molecular structure consisting of an aliphatic hydrocarbon chain wherein the guanidino group

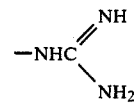

is bonded with the primary carbon atoms existing at the both ends thereof, and having an amino group bonded with the center carbon atom of the molecular chain.

These novel compounds can be effectively utilized as the fungicide possessing a high fungicidal activity against plant diseases without substantially imparting damage to the plants.

2 Claims, No Drawings

GUANIDINE DERIVATIVES

FIELD OF THE INVENTION

The present invention relates to novel guanidine derivatives which can be effectively used as the fungicide to the plant which shows high fungicidal activity against many kinds of plant diseases such as pear black spot. Alternaria leaf spot of apple. Alternaria black spot of strawberry, tobacco brown spot and black spot of apple with substantially no phytotoxicity to plant.

DESCRIPTION OF THE PRIOR ART

It has been known that the guanidino compounds can be the effective fungicide against the plant diseases particularly caused by fungi.

For example, in the prior arts, the guanidino compound having the following formula was well used as such a fungicide.

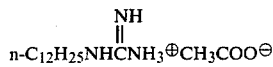

This guanidino compound, however, has the defects that it does not possess a sufficient antifungal property and it brings about high order of phytotoxicity to the plant if it is used in a high concentration so as to attain a sufficient antifungal effect. In particular, the latter is to be decisive because according to the general method of usage fungicide is sprayed to the plant in the state of solution, dispersion, or emulsion and thereafter the concentration of guanidino compound as the fungicide on the plant becomes extremely high by evaporation of the solvent. According to Japanese Patent Publication No. 42-16607, it is also known that di(8-guanidino octyl)amine possesses an antifungal property for the plant.

But this compound cannot be said to be satisfactory in view of both fungicidal activity and phytotoxicity to the plant.

DISCLOSURE OF THE INVENTION

The first object of the present invention is to provide novel guanidine derivatives which can be effectively utilized as such a fungicide as possessing a high fungicidal activity against the plant diseases and, at the same time, having substantially no phytotoxicity to the plant.

The second object of the present invention is to provide the novel guanidine derivatives which can be effectively utilized as the fungicide possessing a high fungicidal activity especially against plant diseases such as pear black spot. Alternaria leaf spot of apple. Alternaria black spot of strawberry, tobacco brown spot and black spot of apple without substantially imparting damage to the plants thereof.

It has now been found that the objects of the present invention can be effectively attained by the novel guanidine derivatives selected from the group consisting of the compound having the following formula (I) and the acid adducts thereof.

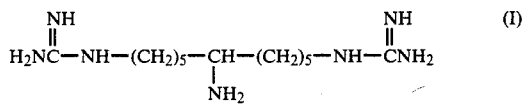

Further, it has been found that the objects of the present invention can be more effectively attained by acid adducts of the compound having the above formula (I) derived from an acid selected from sulfuric acid, acetic acid, or hydrochloic acid.

DESCRIPTION OF THE PREFERRED EMBODIMENT OF THE INVENTION

At first a process for producing the guanidine derivatives of the present invention, subsequently said guanidine derivatives themselves, and finally the fungicidal activity of said guanidine derivatives, are described.

The guanidine derivatives of the present invention are provided by reacting 1,6,11-triaminoundecane with isothiourea derivatives respresented by the following formula (II).

wherein R represents lower alkyl, benzyl, and aralkyl.

This reaction is shown in the following reaction formula (III).

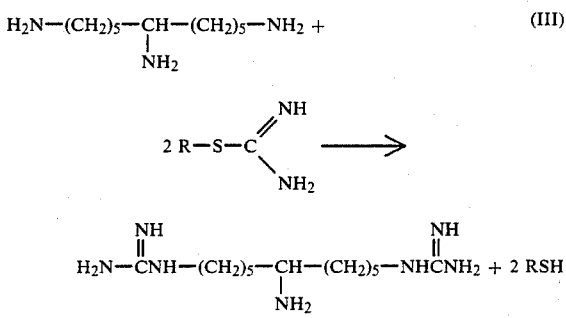

The isothiourea derivative represented by the above formula (II) is subjected to the reaction in the state of the salt thereof with strong acid such as sulfuric acid, nitric acid, hydrochloric acid, carbonic acid, formic acid, acetic acid, propionic acid, oxalic acid, furmaric acid, or citric acid.

S-methylisothiourea sulfate out of isothiourea derivatives is most preferably used.

1,6,11-triaminoundecane can be prepared by the conventional methods, for example by heating ε-caprolactam at a temperature higher than 300° C. in the presence of a strong base selected from oxides or hydroxides of alkali metal or alkaliearth metal to form 7-(5'-aminopentyl)-3,4,5,6-tetrahydro-2H-azepin and thereafter subjecting it to hydrogenation in an aqueous ammonium solution. (Japanese Patent Publication No. 41-18087 specification).

In the reaction for producing the guanidine derivative of the present invention the mole ratio of 1,6,11-triaminoundecane to the isothiourea derivative is not limited but is preferably from a half to one-third.

This reaction can be carried out either in the presence or in the absence of the solvent. As a suitable solvent for the reaction there can be used water, alcohols such as methanol, ethanol, propanol, ethers such as dioxane, tetrahydrofuran, ketones such as acetone, methylethylketone, and acetic acid.

The reaction is carried out, for example, in the manner that 1,6,11-triaminoundecane is dissolved into approximately ten times of alcohol and on the other hand S-methylisothiourea sulfate is dissolved into approximately six times of water, and the former resulting solution is gradually dropped into the latter resulting solution, and simultaneously or thereafter the reaction system is agitated.

The reaction may be carried out at a temperature within the range from room temperature to the boiling point of the solvent used.

It is preferable to start the reaction at a room temperature and complete the reaction by heating the reaction system up to the boiling point of the solvent used.

The reaction pressure is not limited but is preferably at atmospheric pressure.

After the reaction is finished, the guanidine derivative of the present invention is isolated from the reaction mixture by distilling out the solvent, if necessary, after the reaction mixture is neutralized by adding thereto the mineral acid such as sulfuric acid, hydrochloric acid, and nitric acid or acetic acid.

The resulting acid adducts of guanidine derivative of the present invention can be purified by the recrystalization method.

For example, it is usually an practical way of purification to drop the reaction mixture before distilling out the solvent into a large amount of methanol at a room temperature.

Thus obtained guanidine derivative is a novel compound and a white crystal having 209°–212° C. of melting point in the case of sulfate thereof.

The free guanidine derivative of the present invention is unstable and gradually reacts with carbon dioxide in the air to form a carbonate thereof after a long standing in the air.

Accordingly, when the guanidine derivative of the present invention is subjected to a usage as a fungicide for the plant, it is preferable to keep it in the state of a stable acid adduct.

It makes no difference in the effectiveness of the fungicide which the guanidine derivative is free or in the state of acid adduct.

If the isothiourea derivative as a raw material is used in the form of acid adduct, the resulting product of the present invention can be obtained in the form of the corresponding acid adduct of the guanidine derivative.

There may be used for providing an acid adduct of guanidine derivative the acids such as sulfuric acid, nitric acid, hydrochloric acid, carbonic acid, formic acid, acetic acid, propionic acid, oxalic acid, fumaric acid and citric acid. In particular, sulfate, acetate, and hydrochloride out of the acid adducts are to be preferable.

The novel compounds of the present invention are characterized in that they have a molecular structure consisting of an aliphatic hydrocarbon chain wherein the guanidino group

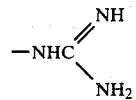

is bonded with the primary carbon atoms existing at the both ends thereof, and they have an amino group bonded with the center carbon atom of the molecular chain.

Two guanidino groups per one molecule can give the excellent antifungal property to the compounds of the present invention, and the suitable length of methylene group altogether with an amino group can impart a suitable value of HLB (Hydrophile-Lipophile-Balance) to the compound, which may result in having the compound possess the excellent antifungal property and the negligible order of phytotoxicity to the plant.

The compounds of the present invention can be used as a fungicide for the plant according to the conventional method in the state of for example, aqueous solution, dispersions, emulsions, wettable powders, dusts, pellets, or pastes after being mixed with carrier or diluent if necessary.

The most characteristic feature of the compounds of the present invention exists in that said compounds can show the fungicidal activity much higher than that of conventional guanidino compounds against the plant diseases caused by pathogenic fungi belonging to Alternaria or Venturia such as pear black spot, tobacco brown spot, leaf spot of apple, black spot of strawberry, and black spot of apple, and they have substantially no phytotoxicity to such plants.

EXAMPLE 1

[Synthesis of 1,11-diguanidino-6-aminoundecane sulfate]

In a three-necked 1 l flask installed with a stirrer, 58.45 g (0.42 mole) of S-methyl-isothiourea sulfate was dissolved in 350 ml of distilled water.

28.21 g (0.14 mole) of 1,6,11-triaminoundecane was dissolved in 350 ml of methanol in a dropping funnel and the dropping funnel was then attached to the above mentioned three-necked flask. It took 40 minutes to add the methanol solution of 1,6,11-triaminoundecane to the aqueous solution of S-methylisothiourea sulfate with stirring at 20°–21° C.

The obtained solution was kept stirring for 2 hours at 20°–21° C. followed by 5.5 hours at 75° C. After cooling down to a room temperature, the obtained solution was dropped to 11.2 l of methanol. The resulting precipitate was gathered by filtration, washed with methanol and then dried for 9 hours at 105° C. under a pressure of 0.5 mmHg.

Thus obtained white crystal was 50.8 g and showed a melting point of 209°–212° C. FIG. 1 shows a result of elementary analysis for the white crystal.

FIG. 1 Elementary Analysis

| | (Structure I, sulfate MW 432) | | | |
|---|---|---|---|---|
| | C | H | N | S |
| observed | 35.9 | 7.9 | 22.7 | 11.0 |
| calculated[1] | 36.1 | 7.9 | 22.7 | 11.1 |

[1] for $H_2N-\underset{\underset{NH}{\|}}{C}-NH-(CH_2)_5-\underset{\underset{NH_2}{|}}{CH}-(CH_2)_5-NH-\underset{\underset{NH}{\|}}{C}-NH_2 \cdot 3/2\ H_2SO_4$ An infrared spectrum for the white crystal showed characteristic IR absorption frequencies of 1100 cm$^{-1}$ for $SO_4^{--}$, 1630–1660 cm$^{-1}$ and 3300 cm$^{-1}$ for a guanidium.

A proton nuclear magnetic resonance ($^1$H-NMR, 60 MHZ) spectrum for a solution of the white crystal in D$_2$O showed characteristic chemical shifts of 1.6 ppm for $-CH_2-$(16H), 3.2–3.4 ppm for $>CH-N<$ and $-CH_2-N<$ (5H), and 4.8 ppm for HDO (13H).

A 22.6 MHZ $^{13}$C-NMR spectrum for the white crystal were assigned as follows:

| NH | | NH$_2$ | | NH | |
|---|---|---|---|---|---|
| ‖ | | \| | | ‖ | |
| H$_2$N—C—NH—(CH$_2$)$_{\overline{5}}$ | | CH—(CH$_2$)$_{\overline{5}}$NH | | —C—NH$_2$·3/2H$_2$SO$_4$ | |
| 157.2 | 24.3 | 52.1 | 24.3 | 157.2 | |
| | 26.0 | | 26.0 | | |
| | 28.0 | | 28.0 | | |
| | 32.0 | | 32.0 | | |
| | 41.4 | | 41.4 | | |
| | | | | (unit ppm) | |

A 400 MHZ $^1$H-HMR spectrum also supported the above chemical structure for the white crystal.

A fast atom bombardment mass spectrum showed peaks at m/z−286 ((MW of structure eI) +1 and m/z−384 ((MW of structure I sulfate)+1)

All these analytical data support [Structure I] for the above obtained white crystal.

EXAMPLE 2

[Preparation of wettable powder]

2.6 g of kaolin was fully crushed and mixed with 0.2 g of silicon dioxide and 0.2 g of polyoxyethylene alkylphenyl ether, a nonion type surfactant, in an agate mortar.

To 0.30 g of the mixed powder, 0.10 g of 1,11-diguanidino-6-aminoundecane sulfate (hereinafter be abbreviated to TUG sulfate) shown in the example 1 was added and thoroughly crushed and mixed in the agate mortar.

The obtained wettable powder was diluted with the distilled water in order to subject it to the testing of effectiveness as a fungicide.

For example, if 0.10 g of this wettable powder is diluted by 100 ml of distilled water, the resulting solution comes to contain 250 ppm of TUG sulfate.

EXAMPLE 3

[Antifungal property against several kinds of Alternaria alternata plant pathogenic fungi]

The antifungal properties of the wettable powder of TUG sulfate which was obtained in the example 2 against several kinds of plant diseases caused by Alternaria alternate pathogenic organisms were measured according to the conventional method. The result is shown in Table 1.

TABLE 1

| The plant to be tested | The kind of disease | The pathogenic organism | The concentration of TUG sulfate (ppm) | The number of disease spot per leaf[1] |
|---|---|---|---|---|
| Japanese pear ("Nijuuseiki") | black spot | Alternaria alternata, Japan pear pathotype | 50<br>10<br>0 | 0<br>21<br>113 |
| apple ("Star king delicious") | leaf spot of apple | Alternaria alternata, apple pathotype | 50<br>10<br>0 | 9<br>37<br>66 |
| tobacco ("Burley 21") | tobacco brown spot | Alternaria alternata, tobacco pathotype | 50<br>10<br>0 | 3<br>25<br>22 |
| strawberry ("Morioka 16") | black spot of strawberry | Alternaria alternata strawberry pathotype | 50<br>10<br>0 | 16<br>48<br>60 |

[1]As for the black spot of strawberry this number was so high that the number of disease spot per 1 cm$^3$ was shown.

EXAMPLE 4

[Fungicidal activity studies in a field against Japanese pear "Nijuuseiki" black spot]

The wettable powders of TUG sulfate prepared in the example 2 were tested against Japanese pear "Nijuuseiki" black spot in a test field. The test started in end week of April, 1983 and ended at the middle of July, 1983. During that period, the water suspension of the wettable powder was sprayed once a 10 days and totally eight times. Percent of diseased leaves was determined at the end of July.

The result is shown in Table 2 along with those of comparative fungicides.

TABLE 2

| Fungicide | Concentration in sprayed water (ppm) | leaves with *[1] black spot (%) |
|---|---|---|
| TUG sulfate | 800 | 47.0 |
| TUG sulfate | 400 | 53.6 |
| 1,11-diguanidinoundecane sulfate *[2] | 400 | 64.5*[3] |
| Dodecylguanidine acetate*[2] | 400 | No measurement was made because of too much phytotoxicity |
| Copper 8-quinolinolate | 670 | 61.1 |

*[1]As for each fungicide, tests were made against three trees. Percent means the mean value given by dividing the number of diseased leaves by the total number of leaves on voluntarily selected ten branches of one tree.
*[2]The wettable powders were prepared in the same manner as in the case of TUG sulfate.
*[3]Phytotoxicity to let fresh leaves shrink was observed.

EXAMPLE 5

(A field study on Phytotoxicity to Japanese pears)

The wettable powders of each fungicide were applied (dispersed) as 200 ppm sprays to flowers and young leaves of Japanese pear "Nijuuseiki", "Shinsui", and "Kousui" at the end of April and at the middle of May. Phytotoxicity was checked with the naked eye.

The result is shown in Table 3 along with those of comparative fungicides.

TABLE 3

| Fungicide | Observation |
|---|---|
| TUG sulfate | No phytotoxicity was observed with respect to both flowers and young leaves. |
| 1,11-diguanidino-undecane sulfate | Phytotoxicity that young leaves shrink was observed |
| Dodecylguanidine acetate | Phytotoxicity that young leaves shrink to a great extent was observed. |

Even when 1,11-diguanidinoundecane sulfate was applied as 100 ppm sprays, the same phytotoxicity was observed.

On the other hand, when TUG sulfate was applied as 800 ppm sprays, no phytotoxicity was observed.

EXAMPLE 6

(Synthesis of 1,11-diguanidino-6-aminoundecane acetate and testing of its antifungal property)

To a three-necked 100 ml flask installed with a stirrer, 4.03 g (0.02 mole) of 1,6,11-triaminoundecane, 5.37 g (0.04 mole) of o-methylisourea acetate, and 16.0 g of water was supplied, and it was reacted for 16 hours with stirring at 22°–23° C. After the reaction was finished, 1.50 g of acetic acid was added into the reaction mixture to let it show pH 6.5.

The reaction mixture was concentrated and dried to form 9.65 g of transparent paste-like solid.

This paste-like solid was crystalized by adding thereto 300 ml of acetone, and then crushed in the agate mortar, and filtrated, followed by drying.

Thus obtained white crystal have a melting point of 46°–49° C.

FIG. 2 shows a result of elementary analysis for the white crystal.

| [Structued II, actate MW 465] | | | |
|---|---|---|---|
| | FIG. 2 Elementary Analysis | | |
| | C | H | N |
| Calculated[1] | 49.0 | 9.3 | 21.1 |
| Observed | 48.6 | 9.7 | 19.8 |

[1] for $H_2N-\underset{\underset{NH}{\|}}{C}-NH-(CH_2)_5-\underset{\underset{NH_2}{|}}{CH}-(CH_2)_5-NH-\underset{\underset{NH}{\|}}{C}-NH_2 \cdot 3\ CH_3COOH$ An infrared spectrum for the white crystal showed characteristic IR absorption frequencies of 1630–1660 $cm^{-1}$ and 3300 $cm^{-1}$ for a guanidium.

A proton nuclear magnetic resonance ($^1$H-NMR) spectrum for a solution of the white crystal in $D_2O$ showed characteristic chemical shift of 1.6 ppm for $-CH_2-(16H)$, 1.94 ppm for $CH_3COO(9H)$, 3.2–3.4 ppm for $>CH-N<$ and $-CH_2-N<(5H)$, and 4.8 ppm for HDC (13H).

A fast atom bombardment mass spectrum showed a peak at $m/z=286$.

All these analytical data support [structure II] for the above obtained white crystal.

The wettable powder of this compound, that is, 1,11-diguanidino-6-aminoundecane acetate was prepared according to the method described in the example 2 and was diluted with water to prepare two aqueous solutions thereof, one having 10 ppm of concetration of said compound and the other having 50 ppm of said compound. Fungicidal activity of these solutions against pear black apots was studies according to the conventional method. The result is shown in in the following:

| Concentration of 1,11-diguanidino-6-amino-undecane acetate (ppm) | Number of diseased spot per leaf |
|---|---|
| 50 | 1 |
| 10 | 16 |
| 0 | 127 |

INDUSTRIAL UTILIZABILITY

The novel guanidine derivatives of the present invention can be utilized as fungicides for the plant.

We claim:

1. Guanidine derivatives having the following formula (I) and acid adducts thereof.

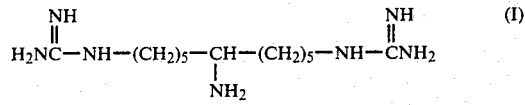

2. Guanidine derivatives described in claim 1 wherein said acid adducts are seleted from the group consisting of sulfate, acetate, and hydrochloride.

* * * * *